US009386986B2

(12) United States Patent
White et al.

(10) Patent No.: US 9,386,986 B2
(45) Date of Patent: Jul. 12, 2016

(54) STAPLE AND FEEDER BELT CONFIGURATIONS FOR SURGICAL STAPLER

(71) Applicant: Cardica, Inc., Redwood City, CA (US)

(72) Inventors: Nathan H. White, Longmont, CO (US); Michael P. Schaller, Palo Alto, CA (US); Michael Murillo, Palo Alto, CA (US); Jared L. Van Cleave, Menlo Park, CA (US); Philipe R. Manoux, San Francisco, CA (US); Bryan D. Knodel, Flagstaff, AZ (US); Benjamin J. Matthias, San Mateo, CA (US); John E. Rivera, Woodside, CA (US)

(73) Assignee: Cardica, Inc., Redwood City, CA (US)

( * ) Notice: Subject to any disclaimer, the term of this patent is extended or adjusted under 35 U.S.C. 154(b) by 622 days.

(21) Appl. No.: 13/746,449

(22) Filed: Jan. 22, 2013

(65) Prior Publication Data

US 2013/0126585 A1 May 23, 2013

Related U.S. Application Data

(60) Continuation of application No. 13/282,759, filed on Oct. 27, 2011, which is a division of application No. 12/477,834, filed on Jun. 3, 2009, now Pat. No. 8,056,789, application No. 13/746,449, which is a (Continued)

(51) Int. Cl.
*A61B 17/068* (2006.01)
*A61B 17/072* (2006.01)
*A61B 17/064* (2006.01)

(52) U.S. Cl.
CPC ......... *A61B 17/07207* (2013.01); *A61B 17/068* (2013.01); *A61B 17/0644* (2013.01); *A61B 2017/07228* (2013.01); *A61B 2017/07278* (2013.01)

(58) Field of Classification Search
CPC ................ A61B 17/07207; A61B 17/0544; A61B 17/068; A61B 2017/07242; A61B 2017/07235; A61B 2017/07228; A61B 2017/0725; A61B 2017/07264
USPC ................................ 227/175.1, 176.1–178.1
See application file for complete search history.

(56) References Cited

U.S. PATENT DOCUMENTS

| 3,581,551 A | 6/1971 | Wilkinson |
| 3,650,453 A | 3/1972 | Smith, Jr. |

(Continued)

FOREIGN PATENT DOCUMENTS

| EP | 1238634 | 9/2002 |
| EP | 1464287 | 10/2004 |

(Continued)

OTHER PUBLICATIONS

"Cardica Microcutter Implant Delivery Device (501)k", Cover Sheet, Table 10.1, "Substantial Equivalence Comparison", and Section 12, "Substantial Equivalence Discussion", Oct. 18, 2012.

(Continued)

*Primary Examiner* — Michelle Lopez
(74) *Attorney, Agent, or Firm* — Womble Carlyle Sandridge & Rice LLP

(57) ABSTRACT

One exemplary surgical apparatus may include at least one carrier, staples fixed to a corresponding carrier, and a feeder belt to which at least one carrier is frangibly connected. Another exemplary surgical apparatus may include a feeder belt, a first plurality of staples fixed directly to and frangibly separable from the feeder belt; a plurality of extension arms extending at least partially in the lateral direction away from the feeder belt; and a second plurality of staples each fixed to an extension arm at a location spaced laterally apart from the feeder belt.

20 Claims, 14 Drawing Sheets

Related U.S. Application Data continuation of application No. 13/090,168, filed on Apr. 19, 2011, now Pat. No. 8,365,973, which is a continuation of application No. 12/477,834, filed on Jun. 3, 2009, now Pat. No. 8,056,789.

(56) References Cited

U.S. PATENT DOCUMENTS

| | | | |
|---|---|---|---|
| 3,899,914 | A | 8/1975 | Akiyama |
| 4,086,926 | A | 5/1978 | Green et al. |
| 4,179,057 | A | 12/1979 | Becht et al. |
| 4,228,895 | A | 10/1980 | Larkin |
| 4,375,866 | A | 3/1983 | Giersch et al. |
| 4,391,402 | A | 7/1983 | Campbell et al. |
| 4,475,679 | A | 10/1984 | Fleury, Jr. |
| 4,556,058 | A | 12/1985 | Green |
| 4,573,625 | A | 3/1986 | Olesen et al. |
| 4,583,276 | A | 4/1986 | Olesen |
| 4,589,416 | A | 5/1986 | Green |
| 4,633,861 | A | 1/1987 | Chow et al. |
| 4,762,260 | A | 8/1988 | Richards et al. |
| 4,807,628 | A | 2/1989 | Peters et al. |
| 4,951,860 | A | 8/1990 | Peters et al. |
| 4,969,591 | A | 11/1990 | Richards et al. |
| 4,996,820 | A | 3/1991 | Harrison, Jr. |
| 5,027,834 | A | 7/1991 | Pruitt |
| 5,156,315 | A | 10/1992 | Green et al. |
| 5,192,288 | A | 3/1993 | Thompson et al. |
| 5,221,036 | A | 6/1993 | Takase |
| 5,413,272 | A | 5/1995 | Green et al. |
| 5,476,506 | A | 12/1995 | Lunn |
| 5,655,698 | A | 8/1997 | Yoon |
| 5,662,260 | A | 9/1997 | Yoon |
| 5,692,668 | A | 12/1997 | Schulze et al. |
| 5,810,855 | A | 9/1998 | Rayburn et al. |
| 5,816,471 | A | 10/1998 | Plyley et al. |
| 5,833,695 | A | 11/1998 | Yoon |
| 5,855,311 | A | 1/1999 | Hamblin et al. |
| 5,894,979 | A | 4/1999 | Powell |
| 5,918,791 | A | 7/1999 | Sorrentino et al. |
| 5,964,774 | A | 10/1999 | McKean et al. |
| 6,306,149 | B1 | 10/2001 | Meade |
| 6,391,038 | B2 | 5/2002 | Vargas et al. |
| 6,602,252 | B2 | 8/2003 | Mollenauer |
| 6,716,232 | B1 | 4/2004 | Vidal et al. |
| 6,817,508 | B1 | 11/2004 | Racenet et al. |
| 6,843,403 | B2 | 1/2005 | Whitman |
| 6,994,714 | B2 | 2/2006 | Vargas et al. |
| 7,025,747 | B2 | 4/2006 | Smith |
| 7,055,730 | B2 | 6/2006 | Ehrenfels et al. |
| 7,097,089 | B2 | 8/2006 | Marczyk |
| 7,140,527 | B2 | 11/2006 | Ehrenfels et al. |
| 7,168,604 | B2 | 1/2007 | Milliman et al. |
| 7,172,104 | B2 | 2/2007 | Scirica et al. |
| 7,179,267 | B2 | 2/2007 | Nolan et al. |
| 7,207,471 | B2 | 4/2007 | Heinrich et al. |
| 7,213,736 | B2 | 5/2007 | Wales et al. |
| 7,225,963 | B2 | 6/2007 | Scirica |
| 7,225,964 | B2 | 6/2007 | Mastri et al. |
| 7,234,624 | B2 | 6/2007 | Gresham et al. |
| 7,238,195 | B2 | 7/2007 | Viola |
| 7,918,376 | B1 | 4/2011 | Knodel et al. |
| 7,918,873 | B2 | 4/2011 | Cummins |
| 7,934,630 | B2 | 5/2011 | Shelton, IV et al. |
| 7,934,631 | B2 | 5/2011 | Balbierz et al. |
| 8,205,780 | B2 | 6/2012 | Sorrentino et al. |
| 8,365,973 | B1 | 2/2013 | White et al. |
| 8,365,976 | B2 | 2/2013 | Hess et al. |
| 8,439,244 | B2 | 5/2013 | Holcomb et al. |
| 2003/0120284 | A1 | 6/2003 | Palacios et al. |
| 2003/0236551 | A1 | 12/2003 | Peterson |
| 2005/0184121 | A1 | 8/2005 | Heinrich |
| 2006/0011699 | A1 | 1/2006 | Olson et al. |
| 2006/0041273 | A1 | 2/2006 | Ortiz et al. |
| 2006/0151567 | A1 | 7/2006 | Roy |
| 2007/0027472 | A1 | 2/2007 | Hiles et al. |
| 2007/0034668 | A1 | 2/2007 | Holsten et al. |
| 2007/0073341 | A1 | 3/2007 | Smith et al. |
| 2007/0083234 | A1 | 4/2007 | Shelton, IV et al. |
| 2007/0118163 | A1 | 5/2007 | Boudreaux et al. |
| 2007/0125828 | A1 | 6/2007 | Rethy et al. |
| 2007/0175950 | A1 | 8/2007 | Shelton, IV et al. |
| 2007/0194079 | A1 | 8/2007 | Hueil et al. |
| 2008/0078802 | A1 | 4/2008 | Hess et al. |
| 2008/0078807 | A1 | 4/2008 | Hess et al. |
| 2008/0078808 | A1* | 4/2008 | Hess et al. ............... 227/181.1 |
| 2009/0065552 | A1 | 3/2009 | Knodel et al. |
| 2010/0230464 | A1 | 9/2010 | Knodel et al. |
| 2012/0080497 | A1* | 4/2012 | White et al. ............. 227/177.1 |

FOREIGN PATENT DOCUMENTS

| | | |
|---|---|---|
| EP | 1736104 | 12/2006 |
| EP | 2060234 | 5/2009 |
| JP | 2005160933 | 6/2005 |
| RU | 2080833 | 6/1997 |
| WO | 8101953 | 7/1981 |
| WO | 8501427 | 4/1985 |
| WO | WO 8904146 | 5/1989 |
| WO | WO 2008118728 | 10/2008 |

OTHER PUBLICATIONS

Gong, Shao Wei, "Perfectly flexible mechanism and integrated mechanism system design", Mechanism and Machine Theory, Jun. 17, 2004.

Kolios, MD, et al. "Microlaparoscopy", Journal of Endourology, vol. 18, No. 9, Nov. 2004.

Lim, Jonas J.B. et al. "A review of mechanism used in laparoscopic surgical instruments", Mechanism and Machine Theory, 38, Feb. 25, 2003.

Lim, Jonas J.B. et al. "Application of Type Synthesis Theory to the Redesign of a Complex Surgical Instrument", Journal of Biomechanical Engineering, vol. 124, Jun. 2002.

Lim, Jyue Boon, "Type Synthesis of a Complex Surgical Device", University of Minnesota Thesis, Feb. 21, 2001.

Steichen, et al. "Mechanical Sutures in Surgery" British Journal of Surgery, vol. 60, No. 3, Mar. 1973, pp. 191-197.

International Search Report and Written Opinion, PCT/US2014/048168, mailed Apr. 9, 2015.

\* cited by examiner

STAPLE AND FEEDER BELT CONFIGURATIONS FOR SURGICAL STAPLER

CROSS-REFERENCE TO RELATED APPLICATIONS

This patent application is a continuation application of U.S. patent application Ser. No. 13/282,759 filed on Oct. 27, 2011, which is a divisional application of U.S. patent application Ser. No. 12/477,834 filed on Jun. 3, 2009, which has been issued as U.S. Pat. No. 8,056,789. This patent application is also continuation application of U.S. patent application Ser. No. 13/090,168 filed on Apr. 19, 2011, which is a continuation application of U.S. patent application Ser. No. 12/477,834 filed on Jun. 3, 2009, which has been issued as U.S. Pat. No. 8,056,789. The contents of the aforementioned related applications are incorporated herein by reference in their entireties.

FIELD OF THE INVENTION

The invention generally relates to surgical staplers and stapling.

BACKGROUND

An endocutter is a surgical tool that staples and cuts tissue to transect that tissue while leaving the cut ends hemostatic. An endocutter is small enough in diameter for use in minimally invasive surgery, where access to a surgical site is obtained through a trocar, port, or small incision in the body. A linear cutter is a larger version of an endocutter, and is used to transect portions of the gastrointestinal tract. A typical endocutter receives at its distal end a disposable single-use cartridge with several rows of staples, and includes an anvil opposed to the cartridge. During actuation of an endocutter, the cartridge fires all of the staples that it holds. In order to deploy more staples, the endocutter must be moved away from the surgical site and removed from the patient, after which the old cartridge is exchanged for a new cartridge. The endocutter is then reinserted into the patient. However, it can be difficult and/or time-consuming to located the surgical site after reinsertion. Further, the process of removing the endocutter from the patient after each use, replacing the cartridge, and then finding the surgical site again is tedious, inconvenient and time-consuming, particularly where a surgical procedure requires multiple uses of the endocutter. That inconvenience may discourage surgeons from using the endocutter for procedures in which use of an endocutter may benefit the patient. Similar inconveniences may accompany the use of surgical staplers other than endocutters.

BRIEF DESCRIPTION OF THE DRAWINGS

The use of the same reference symbols in different figures indicates similar or identical items.

DETAILED DESCRIPTION

Figure 1:
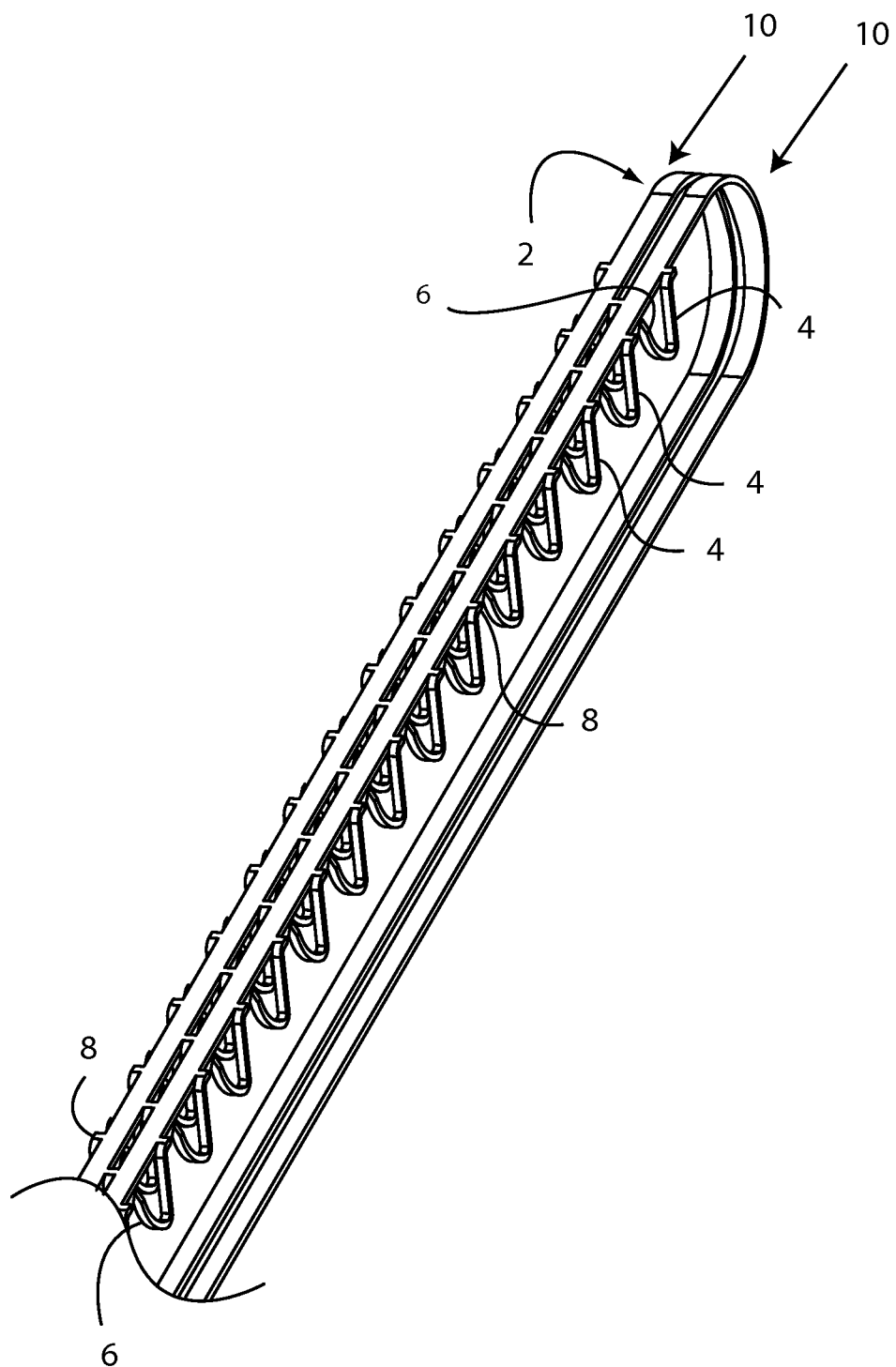
FIG. 1 is a perspective view of an exemplary feeder belt with staples affixed thereto.

U.S. patent application Ser. No. 12/263,171, filed on Oct. 31, 2008 (the "Endocutter Document"), is hereby incorporated by reference herein in its entirety. The Endocutter Document describes exemplary feeder belts used in a surgical stapler. Referring to FIG. 1, a feeder belt 2 may be a long, narrow, thin strip of material from which one or more staples 4 extend. The feeder belt 2 and staples 4 of the present document may be substantially as set forth in the Endocutter Document, with the exception of the inventive features set forth in the present document. Each staple 4 may have a free end 6, and an opposite end 8 that is connected to the feeder belt 2. Advantageously, the staples 4 are frangibly affixed to the feeder belt 2, such that they are sheared off from the feeder belt 2 during deployment. However, the staples 4 may be connected to the feeder belt 2 in any suitable manner. One or more rows 10 of staples 4 may be connected to the feeder belt 2. Each row 10 of staples 4 is the group of staples 4 positioned at substantially the same lateral location relative to the longitudinal centerline of the feeder belt 2, and each row 10 of staples 4 may be oriented generally longitudinally. After deployment, each staple 4 may form substantially a D-shape. As seen in FIG. 1, an exemplary feeder belt 2 may be a generally flat and generally linear piece of material that carries a plurality of staples 4. The feeder belt 2 may lie substantially in a single plane. The feeder belt 2 may be flexible, or instead may be rigid.

Figure 2:
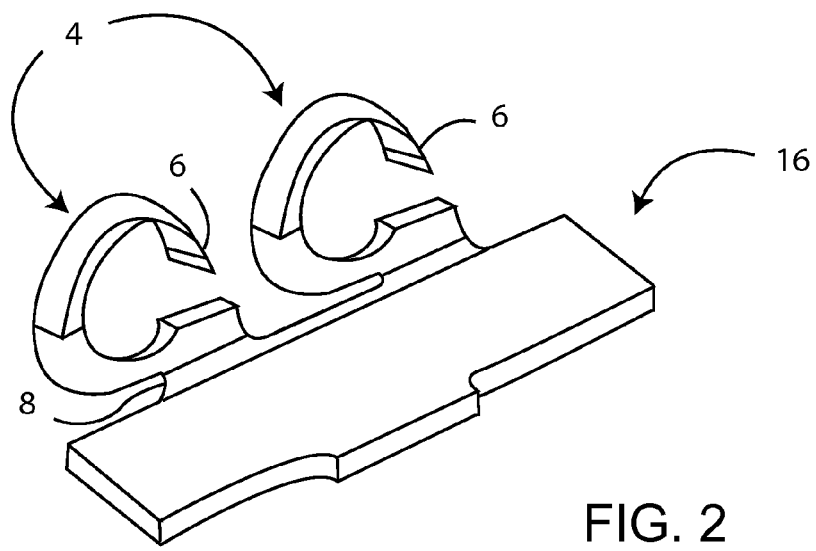
FIG. 2 is a perspective view of a carrier with staples affixed thereto.
Figure 3:
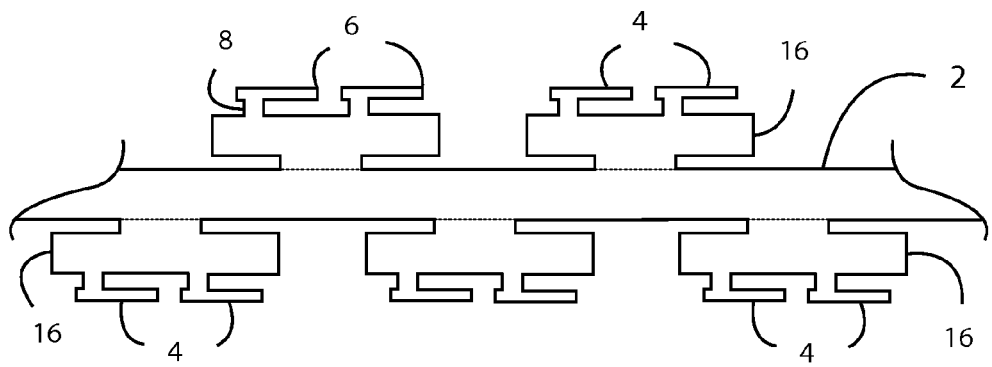
FIG. 3 is a top view of carriers and staples of FIG. 2 attached to an exemplary feeder belt.

Referring also to FIGS. 2-3, at least two staples 4 may be generally D-shaped, and may extend from a carrier 16. This configuration of staples 4 may be referred to as the "double-D configuration." The end 8 of each staple 4 that is connected to the carrier 16 may be fixed to that carrier 16 such that the staples 4 are not frangibly separable from the carrier 16. Instead, the carrier 16 may itself be fixed to and frangibly separable from the feeder belt 2. In this way, the carrier 16 is implanted in tissue along with the attached staples 4. The connection between the carrier 16 and the feeder belt 2 may be coined or otherwise fabricated to facilitate frangible separation from the feeder belt 2. Such a connection may be made in the same or similar manner as between a staple 4 and the feeder belt 2 as set forth in the Endocutter Document, or in a different manner. As shown in FIG. 2, staples 4 that are attached to a carrier 16 may be substantially in the same plane as one another, such that the staples 4 all extend from the same side of the carrier 16. Further, those staples 4 may be oriented in substantially the same direction as one another, such that the free end 6 of each staple 4 is located at the proximal end or at the distal end of each staple 4. Alternately, at least one staple 4 attached to a carrier 16 may be oriented in a different direction relative to a least one other staple 4. At least one carrier 16 may be in substantially the same plane as the feeder belt 2, and positioned lateral to the feeder belt 2.

Figure 4:
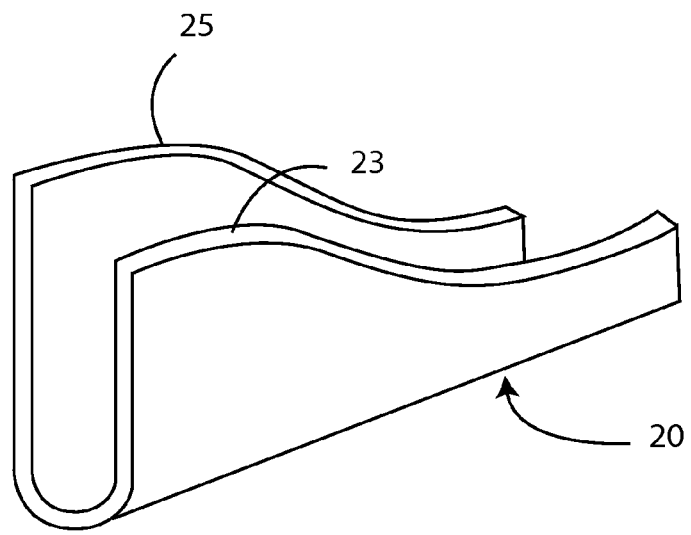
FIG. 4 is a perspective view of an exemplary wedge.

Referring also to FIG. 4, the wedge 20 used to form the staples 4 and then shear the carrier 16 from the feeder belt 2 may have a three-dimensional form. That is, the wedge 20 may include two separate ramps 22, 24, where the first ramp 22 is configured to deform staples 4 and the second ramp 24 is configured to shear the carriers 16 from the feeder belt 2. The wedge 20 may be actuated substantially as described in the Endocutter Document, with the following differences. The first ramp 22 may be located laterally outboard relative to the second ramp 24. As the wedge 20 slides relative to the feeder belt 2, the first ramp 22 sequentially engages staples 4, deforming them upward into contact with an anvil which causes further deformation. The first ramp 22 is shaped to facilitate that deformation, such as set forth in the Endocutter Document. The second ramp 24 may be located laterally inboard relative to the first ramp 22. The second ramp 24 is shaped such that, after the staples 4 attached to a carrier 16 have been deformed by contact with the first ramp 22, the second ramp 24 contacts and exerts a force on the carrier 16 and/or the junction between the feeder belt 2 and that carrier 16 in order to shear off or otherwise separate the carrier 16 from the feeder belt 2. Alternately, instead of a three-dimensional wedge 20 with two separate ramps 22, 24, two separate wedges 20 may be utilized, where one wedge 20 deforms staples 4 and the other wedge 20 shears carriers 16 from the feeder belt 2.

Figure 5:
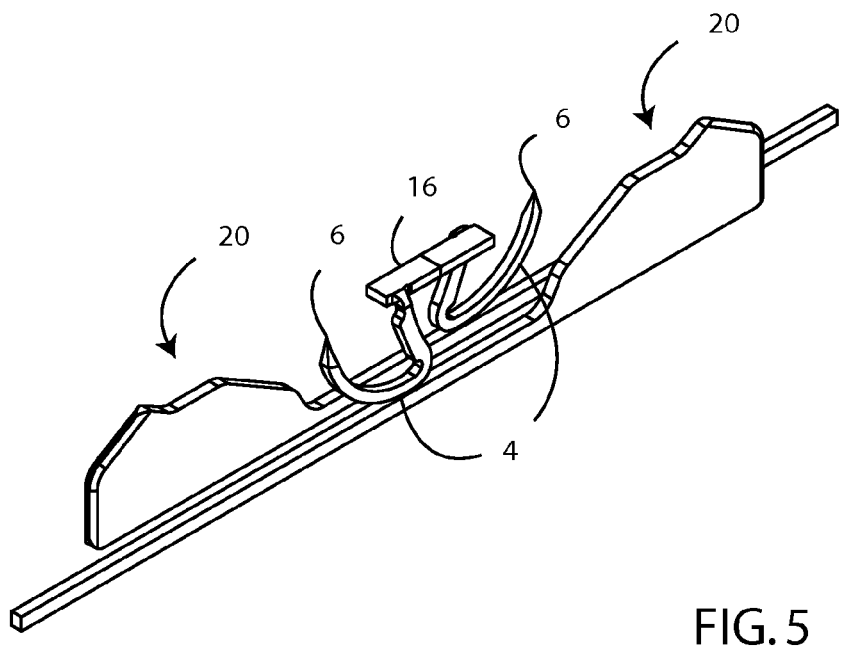
FIG. 5 is a perspective view of another exemplary carrier with staples affixed thereto, prior to deployment.
Figure 6:
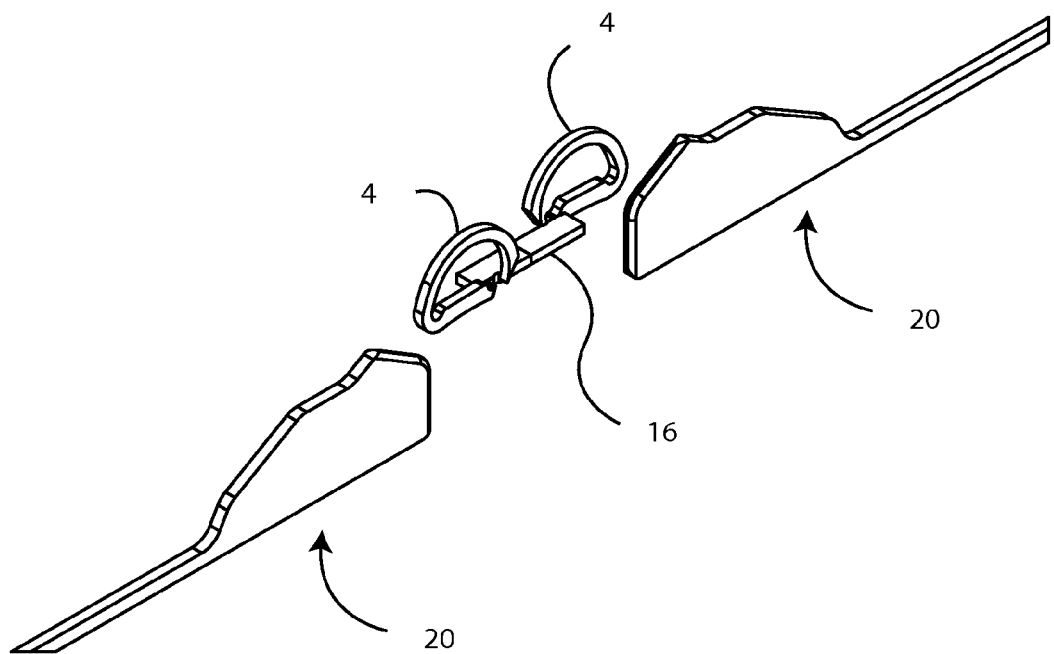
FIG. 6 is the perspective view of FIG. 5, after deployment.

Alternately, at least one staple 4 that is attached to a carrier 16 may be out of plane relative to at least one other staple 4 that is attached to that carrier 16. Referring also to FIG. 5, a carrier 16 may have two or more staples 4 extending therefrom, where at least one staple 4 extends from a different side of the carrier 16 than at least one other staple 4. At least one staple 4 may be oriented in a different direction from at least one other staple 4. For example, as shown in FIG. 5, two staples 4 may be attached to a carrier 16, where the free end 6 of one staple 4 is located at the proximal end of that staple 4, and the free end 6 of the other staple 4 is located at the distal end of that staple 4. This configuration of the staples 4 may be referred to as the "B configuration." Two separate wedges 20 may be utilized in conjunction with the staples 4 and carrier 16. Those two wedges 20 may move in opposite directions relative to one another, referring also to FIG. 6, to deform the staples 4. One of the wedges 20 may be configured substantially as shown in FIG. 4 such that the wedge 20 can both deform one or more staples 4 and shear the carrier 16 from the feeder belt 2. The resultant combination of the deformed staples 4 and carrier 16 may form generally a B-shape. Alternately, both wedges 20 may be configured as set forth in the Endocutter Document, and the staples 4 may be connected to the feeder belt 2 directly instead of to a carrier 16.

Figure 7:
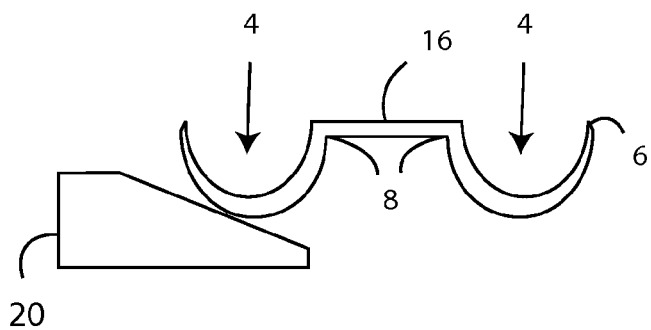
FIG. 7 is a side view of an exemplary staple in a first state.
Figure 8:
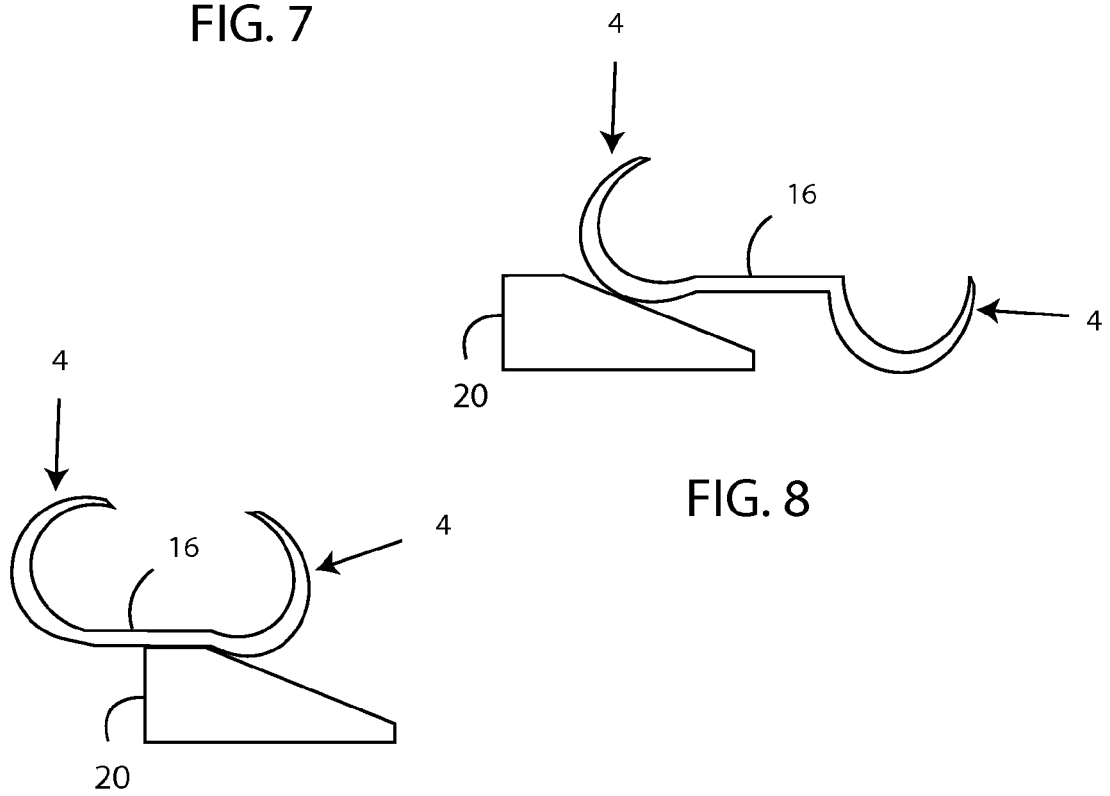
FIG. 8 is a side view of the exemplary staple of FIG. 7 in a second state.
Figure 9:
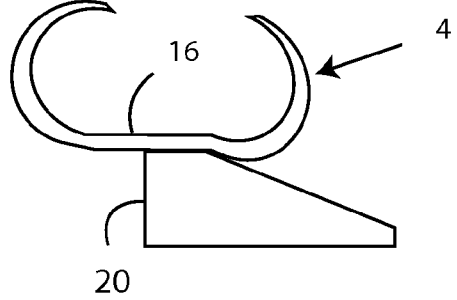
FIG. 9 is a side view of the exemplary staple of FIG. 7 in a third state.
Figure 10:
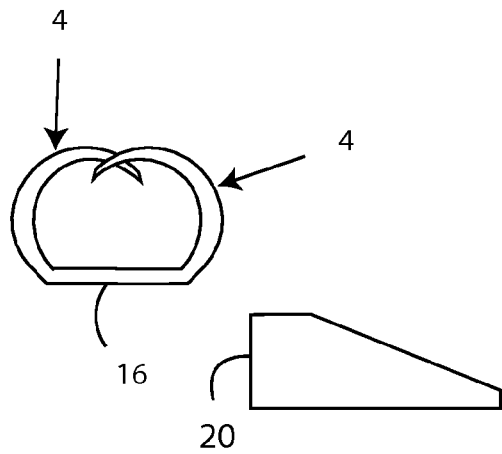
FIG. 10 is a side view of the exemplary staple of FIG. 7 in a fourth, deployed state.

Referring also to FIGS. 7-10, staples 4 may be formed into a B-configuration with a wedge 20 moving in a single direction. Such staples 4 may be attached to a carrier 16 substantially coplanar with one another, similar to the configuration of FIG. 2. As another example, at least two staples 4 may be attached to a carrier 16 out of plane relative to one another, similar to the configuration of FIG. 5. As seen in FIG. 7, at least one staple 4 may be oriented relative to a wedge 20 such that the free end 6 is longitudinally closer to the wedge 20 as it approaches the staple 4 than the opposite end 8. The surface of the wedge 20 that contacts that staple 4, and the staple 4 itself, are shaped such that contact therebetween as the wedge 20 slides relative to the staple 4 urges the free end 6 of the staple 4 upward, referring also to FIG. 8. As the wedge 20 continues to slide relative to the staples 4, the wedge 20 encounters the next longitudinally-successive staple 4, and urges that staple 4 upward as well, referring also to FIG. 9. Optionally, two wedges 20 may be used where at least two staples 4 attached to a carrier 16 are out of plane relative to each other. After the wedge 20 has deformed both staples 4, the staples 4 are in the B-configuration, as shown in FIG. 10. The carrier 16 may then be separated from the feeder belt 2 by the wedge 20. Optionally, the three-dimensional wedge 20 of FIG. 4 may be utilized in order to first form the staples 4 and then separate the carrier 16 from the feeder belt 2.

Figure 11:
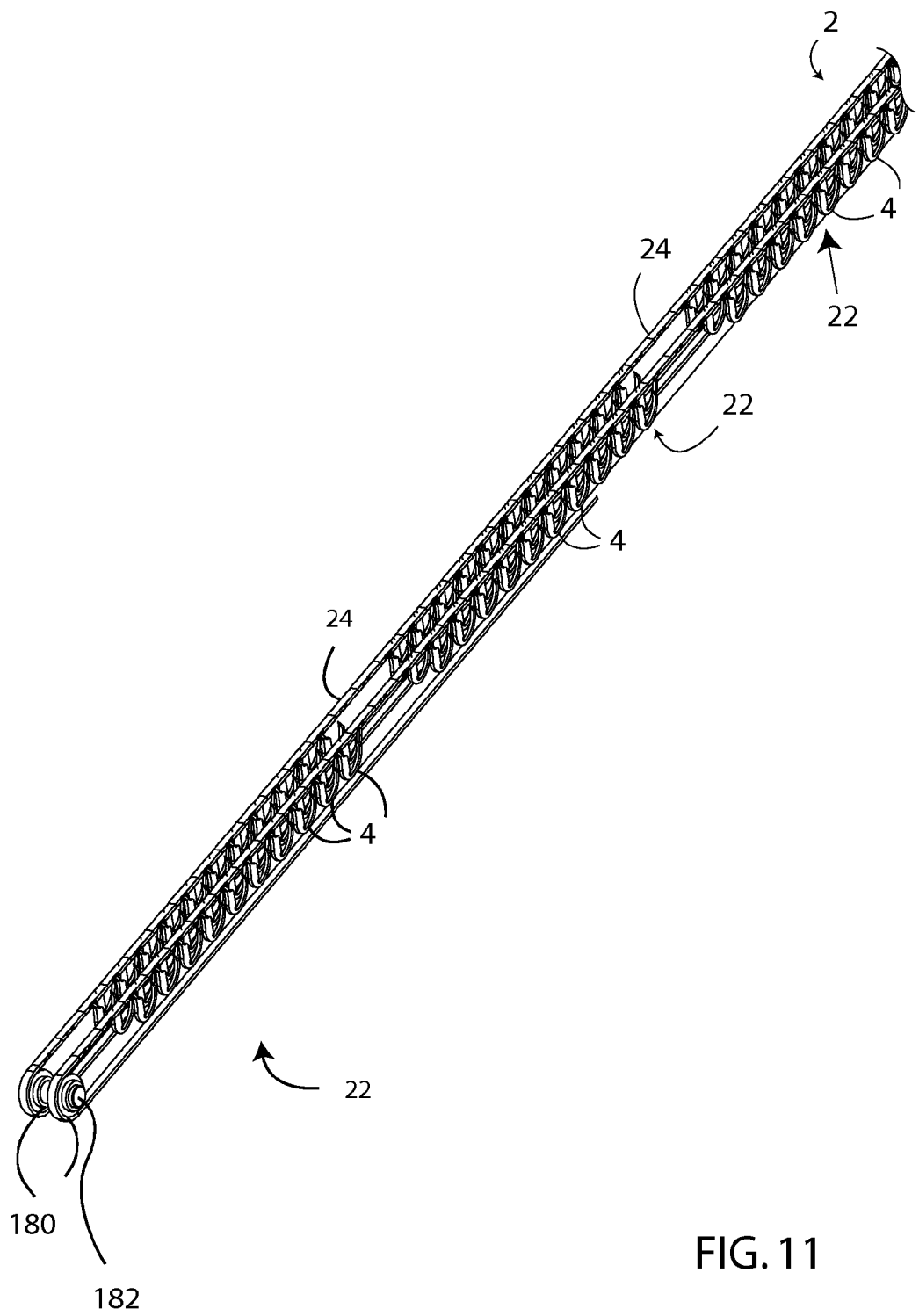
FIG. 11 is a perspective view of an exemplary feeder belt with groups of staples affixed thereto.
Figure 12:
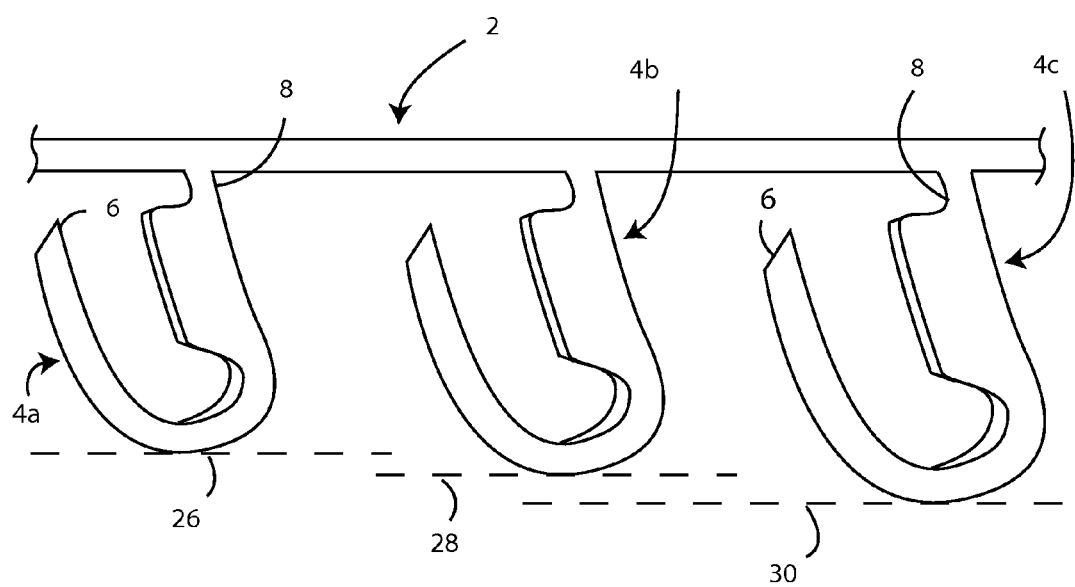
FIG. 12 is a side view of an exemplary feeder belt from which differently-sized staples extend.

The staples 4 may be grouped together along the feeder belt 2 in any suitable manner. As one example, referring also to FIG. 11, the staples 4 may be organized into two or more groups 22 longitudinally spaced apart from one another by blank space 24 along the feeder belt 2. The blank space 24 may have any suitable length. Advantageously, no staples 4 extend from the feeder belt 2 along a blank space 24 on the feeder belt 2. At least one staple 4 may be deployable to a different closed shape than at least one other staple 4. As one example, referring also to FIG. 12, the staples 4 within a group 22 need not be homogeneous. For example, one or more staples 4 may extend downward from the feeder belt 2 a distance greater than one or more other staples 4. A staple 4a may extend downward from the feeder belt 2 a first distance 26. Another staple 4b may extend downward from the feeder belt 2 a second distance 28 greater than the first distance 26. Yet another staple 4c may extend downward from the feeder belt 2 a third distance 30 greater than the second distance 28 The staple 4c may be larger than the staples 4a, 4b. The staples 4a, 4b, 4c may be positioned longitudinally relative to one another in any suitable manner. Advantageously, non-homogeneous staples 4 are positioned longitudinally relative to one another, and differ from one another, in a manner related to a specific surgical procedure to be performed. For example, staple 4a is positioned proximal to staple 4b, which in turn is positioned proximal to staple 4c. In this way, tissue that varies in thickness in a known way may be stapled effectively, where the tissue becomes thicker from the proximal to the distal direction. A staple 4 that extends further downward from the feeder belt 2 may rotate about its attached end 8 substantially the same amount rotationally as a staple 4 extends a lesser distance downward from the feeder belt 2. As a result, the free end of 6 a staple 4c that extends a third distance 30 downward from the feeder belt 2 will swipe through tissue at a height above the feeder belt 2 that is above the height through which the free end of a staple 4*a* extends a first distance 26 downward from the feeder belt 2 can swipe, where the first distance 26 is less than the third distance 30. As another example, one or more staples 4 may be shaped differently from one or more other staples 4, whether or not a subset of those staples 4 extends downward a different distance from the feeder belt 2 than a different subset of those staples 4. As another example, one or more staples 4 within a group 22 may have a D-configuration after formation and shearing, and one or more staples 4 within the same group 22 may have a B-configuration, a double-D configuration, and/or any other suitable configuration. One or more staples 4 within a group 22 may vary from one or more other staples 4 within the same group 22 in any other suitable matter. Alternately, all of the staples 4 within at least one group 22 may be substantially homogeneous.

Figure 13:
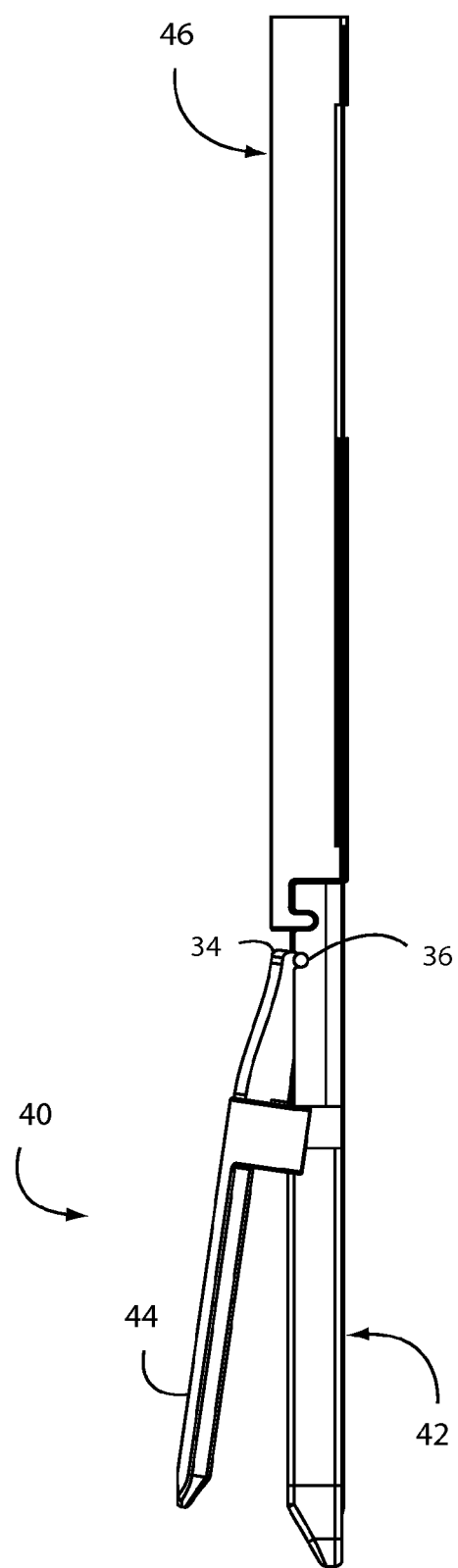
FIG. 13 is a side view of an exemplary surgical instrument with an anvil and staple holder.
Figure 14:
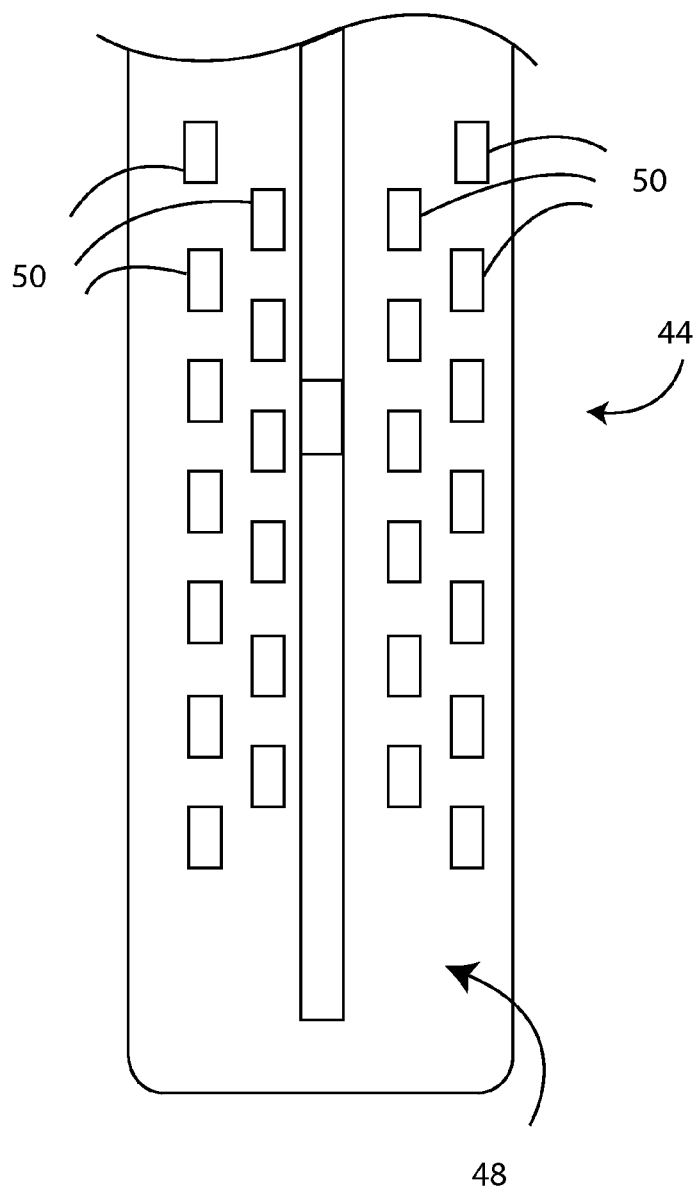
FIG. 14 is a bottom view of an exemplary anvil.

Referring also to FIGS. 13-14, as set forth in the Endocutter Document, a surgical instrument that deploys staples 4 from the feeder belt 2 may include an end effector 40 that includes a staple holder 42 and an anvil 44. One or more feeder belts 2 may extend through a shaft 46 proximal to and connected to the end effector 40, into the staple holder 42. An inner surface 48 of the anvil 44, which is the surface of the anvil 44 oriented generally toward the staple holder 42, may include staple forming pockets 50 defined therein. As the staples 4 are deployed, the free end 6 of each staple 4 may be forced into a corresponding staple forming pocket 50, whereby contact between the free end 6 of that staple 4 and the staple forming pocket 50 causes that staple 4 to close. Each staple forming pocket 50 may be shaped in any suitable manner.

Figure 15:
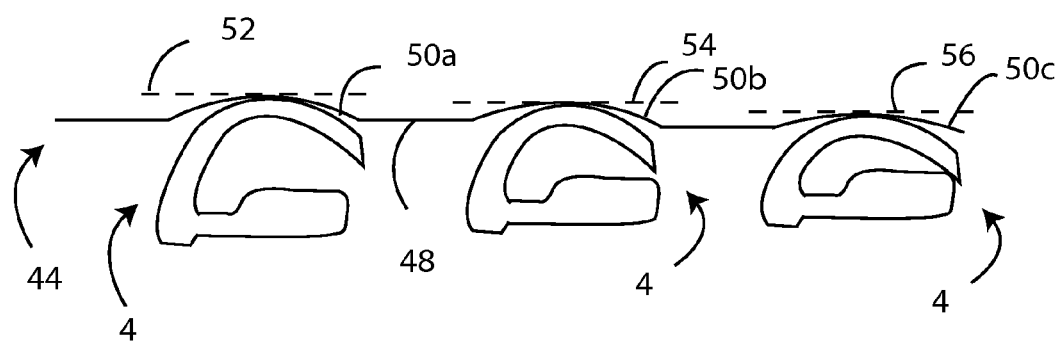
FIG. 15 is a side cross-section view of an anvil with non-homogeneous staple pockets defined therein.

Referring also to FIG. 15, the staple forming pockets 50 need not be homogeneous. As one example, one or more staple forming pockets 50 may extend further into the inner surface 48 of the anvil 44 then one or more other staple forming pockets 50. One anvil forming pocket 50*a* may extend a first distance 52 above the inner surface 48 of the anvil 44. Another anvil forming pocket 50*b* may extend a second distance 54 above the inner surface 48 of the anvil 44, where the second distance 54 may be less than the first distance 52. Another anvil forming pocket 50*c* may extend a third distance 56 above the inner surface 48 of the anvil 44, where the third distance 56 may be less than the second distance 54. As another example, at least one staple forming pocket 50 may be curved or shaped in a different manner than at least one other staple forming pocket 50. For example, one staple forming pocket 50 may have a tighter radius of curvature than a different staple forming pocket 50. As another example, one staple forming pocket 50 may have a complex shape, and another staple forming pocket 50 may simply be arcuate. In this way, different anvil forming pockets 50*a*, 50*b*, 50*c* may form corresponding staples 4 differently. Non-homogeneous anvil forming pockets 50 may be utilized with a feeder belt 2 that utilizes at least one group 22 of staples 4 that is homogeneous, such that different degrees of bending and forming may be applied across a variety of staples 4 that are substantially the same in order to obtain the result of closed staples 4 that are differentially formed. As another example, non-homogeneous anvil forming pockets 50 may be utilized with non homogeneous staples 4, such as those described above, where particular staples 4 are positioned for deployment into particular, corresponding anvil forming pockets 50.

As another example, the inner surface 48 of the anvil 44 need not be flat, such that different anvil forming pockets 50 may be located at a different distance away from the staple holder 42 when the end effector 40 is closed. In this way, staples 4 of different heights may be accommodated. As another example, the gap between the inner surface 48 of the anvil 44 and the staple holder 42 may be adjustable, whether the inner surface 48 is substantially flat or not. In this way, the degree of deformation of the staples 4 within a particular tissue structure held between the anvil 44 and the staple holder 42 may be controlled. The gap may be adjustable in any suitable manner, such as by mechanisms, structures, or methods set forth in co-pending U.S. patent application Ser. No. 12/477,302, filed on Jun. 3, 2009, which is hereby incorporated by reference in its entirety.

Figure 16:
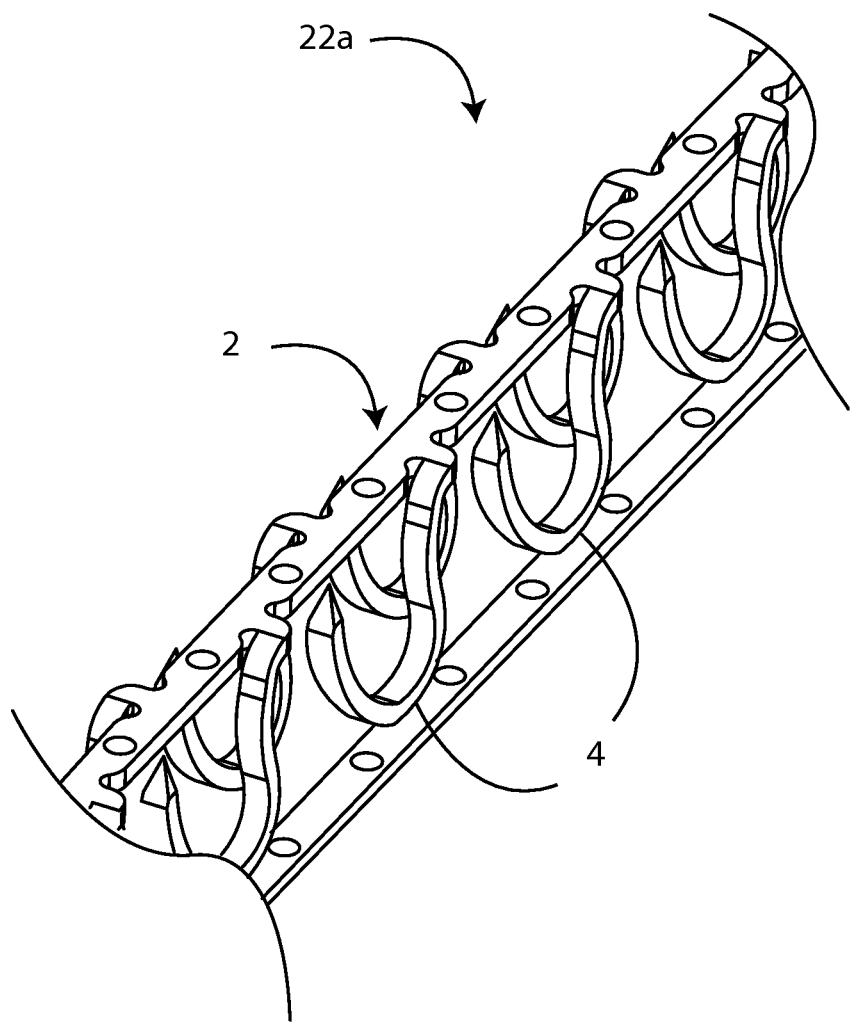
FIG. 16 is a perspective view of a first group of staples extending from a corresponding feeder belt.
Figure 17:
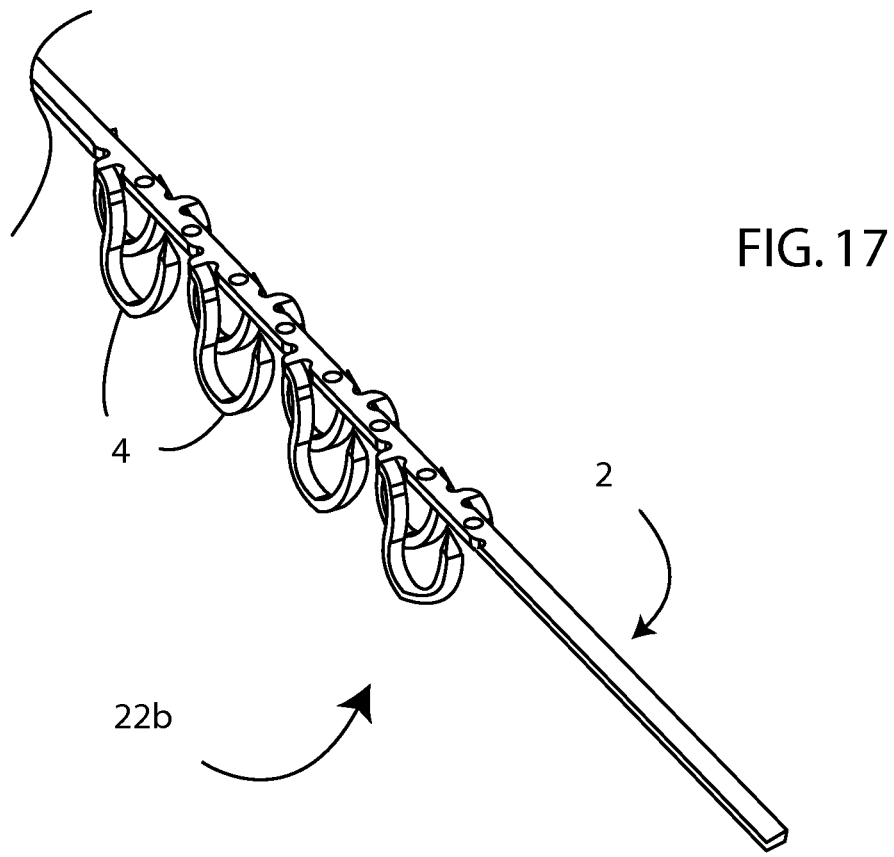
FIG. 17 is a perspective view of a second group of staples extending from the feeder belt of FIG. 16.
Figure 18:
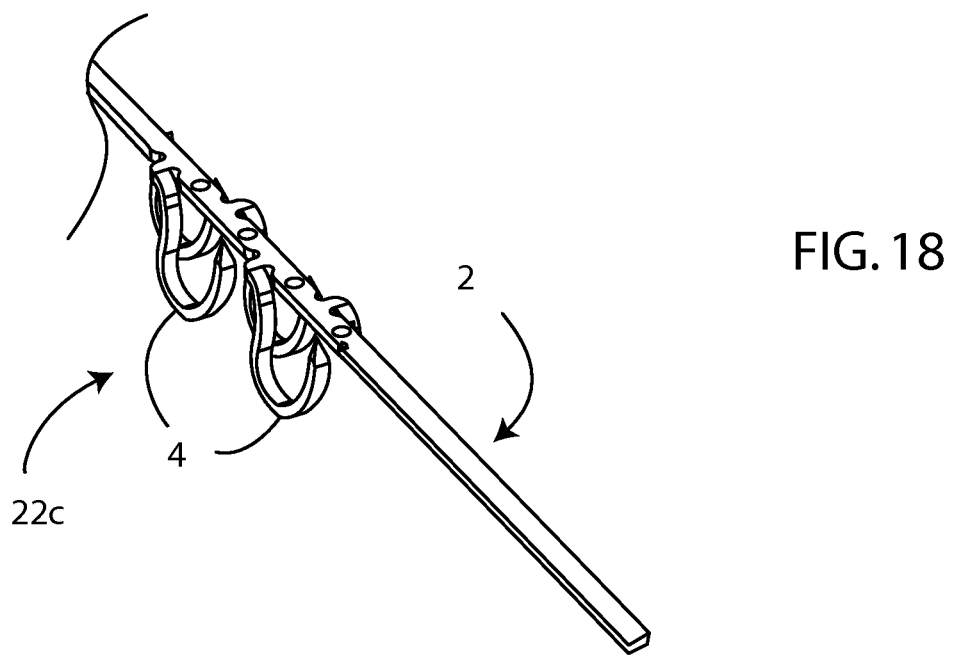
FIG. 18 is a perspective view of a third group of staples extending from the feeder belt of FIG. 16.
Figure 19:
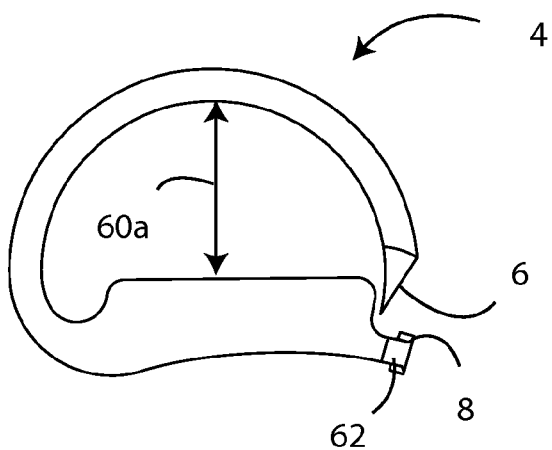
FIG. 19 is a side view of an exemplary variable-thickness staple in a first configuration.
Figure 20:
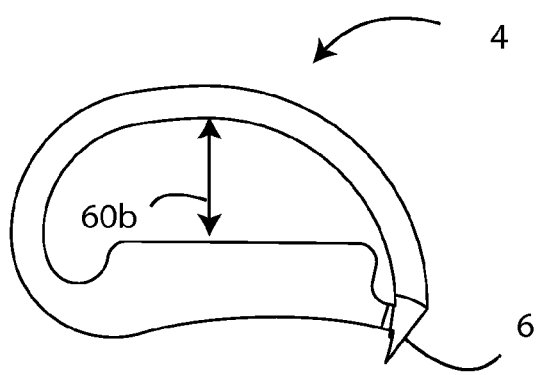
FIG. 20 is a side view of the staple of FIG. 19 in a second configuration.
Figure 21:
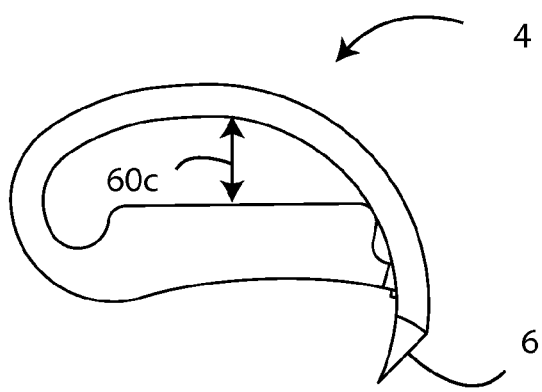
FIG. 21 is a side view of the staple of FIG. 19 in a third configuration.

Referring also to FIGS. 16-18, staples 4 on a feeder belt 2 may form longitudinally-successive groups 22 in which at least one group 22 may have a different number or configuration of staples 4 than at least one other group 22. Such an organization of staples 4 may be advantageous for particular surgical procedures. Referring to FIG. 16, a first group 22*a* of staples 4 may be connected to a feeder belt 2. Referring to FIG. 17, a second group 22*b* of staples 4 may be connected to the feeder belt 2 proximal to the first group 22*a*. The first group 22*a* of staples 4 may include a different number of staples 4 than the second group 22*b*. Referring to FIG. 18, a third group 22*c* of staples 4 may be connected to the feeder belt 2 proximal to the second group 22*b*. The third group 22*c* of staples 4 may include a different number of staples 4 than the first group 22*a* and/or the second group 22*b*. The first group 22*a* is deployed before the second group 22*b*, which in turn is deployed before the third group 22*c*. Where each group 22*a*, 22*b*, 22*c* includes successively fewer staples 4 than the previous one, that configuration of feeder belt 2 may be suitable for a surgical procedure in which tissue structures of increasingly narrow widths are treated with the feeder belt 2.

Where a variable gap between the anvil 44 and staple holder 42 in the closed position of the end effector 40 is provided, the staples 4 may be configured in any manner to take advantage of that variable gap. As one example, referring also to FIGS. 19-21, at least one staple 4 may be configured to be closed through a variety of degrees. Referring to FIG. 19, a staple 4 may be closed to a first degree in which both sides of the staple 4 are closed to a first distance 60*a*. That first distance 60*a* may result from a first gap between the anvil 44 and the staple holder 42. Referring also to FIG. 20, a staple 4 may be closed to a second degree in which both sides of the staple 4 are closed to a second distance 60*b*, which may be less than the first distance 60*a*, and which may result from a second gap between the anvil 44 and the staple holder 42 that is less than the first gap. Referring also to FIG. 21, a staple 4 may be closed to a third degree in which both sides of the staple 4 are closed to a third distance 60*c*, which may be less than the first distance 60*a* and the second distance 60*b*, and which may result from a third gap between the anvil 44 and the staple holder 42 that is less than the first gap and the second gap.

The staple 4 may be configured in any manner to close through a variety of tightnesses 60*a*, 60*b*, 60*c* without causing interference between the free end 6 of the staple 4 and a remainder of the staple 4. As one example, at least one staple 4 may include a notch 62 at or near the end 8 of the staple 4 that is fixed to the feeder belt 2. Such a notch 62 reduces the thickness of the staple 4, such that the free end 6 of the staple 4 can travel within that notch as the staple 4 is closed to a degree in which the free end 6 would otherwise collide and interfere with the staple 4 in the vicinity of the end 8. As another example, at least one staple 4 may be curved laterally such that contact between the free end 6 and a staple-forming pocket causes the free end 6 of the staple 4 to move laterally to and swipe past the other end 8 of the staple 8 as a consequence of the shape of the staple 4. As another example, the shape of at least one staple forming pocket 50 actively deflects the free end 6 of at least one staple 4 laterally, allowing it to swipe past the opposite end 8 of the staple 4 as a consequence of the shape of the staple forming pocket 50. Such a staple-forming pocket 50 alternately may be used in conjunction with a laterally-curved staple 4 such as described immediately above. As another example, the free end 6 of the staple 4 and/or a remainder of the staple 4 may be shaped such that contact between the free end 6 and a remainder of the staple 4 causes the free end 6 to deflect laterally and prevent interference therebetween. To that end, the free end 6 may be conical or otherwise curved, as may a remainder of the staple 4.

Figure 22:
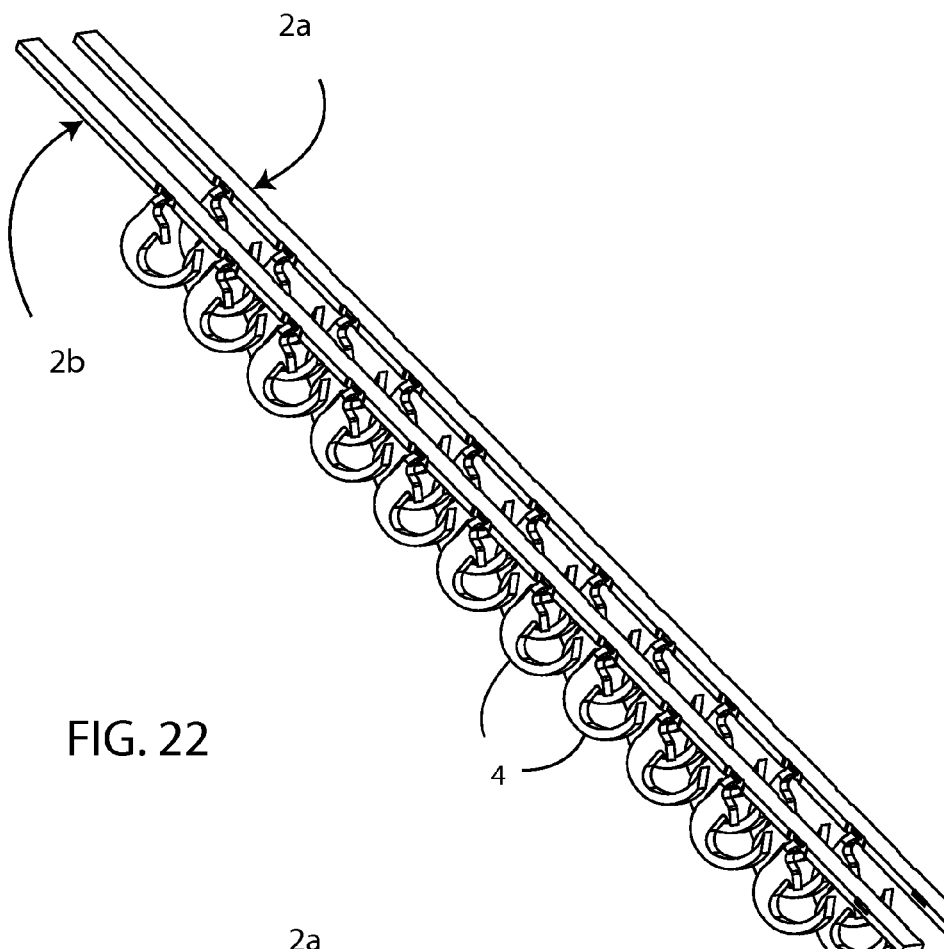
FIG. 22 is a perspective view of two exemplary feeder belts configured to deliver collectively three rows of staples.
Figure 23:
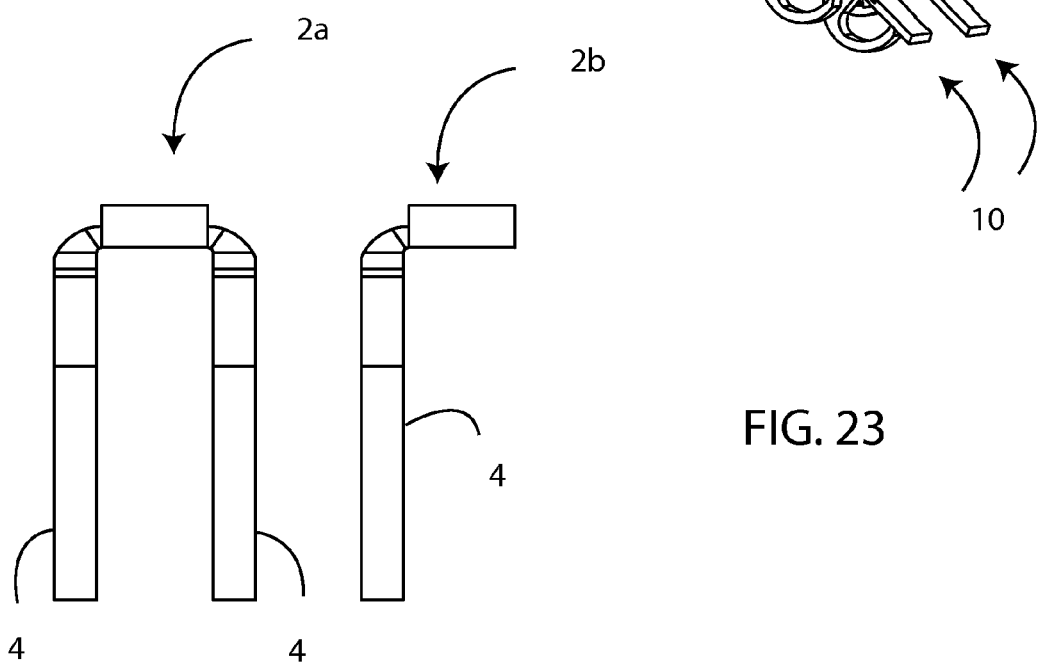
FIG. 23 is an end view of the feeder belts of FIG. 22.

Multiple feeder belts 2 may be utilized in the staple holder 42 in order to provide any suitable number of rows 10 of staples 4 on each side of a knife held by the staple holder 42 that is used for transection or other incision in tissue made by the end effector 40. Referring also to FIGS. 22-23, two feeder belts 2 may be utilized on one or both sides of a transection, where one feeder belt 2a includes two rows 10 of staples 4 such as described above with regard to FIG. 1. The other feeder belt 2b may include a single row 10 of staples 4 configured in any suitable manner. As one example, for ease of fabrication, the feeder belt 2a may be configured in substantially the same way as the feeder belt 2b, where fabrication of a second row 10 of staples 4 is simply omitted from the feeder belt 2b. Alternately, the feeder belt 2b may have any other configuration of staples 4. For example, the staples 4 extending from feeder belt 2b need not be positioned in a row 10, and instead may be laterally staggered relative to one another. Alternately, two feeder belts 2 each may include two rows 10 of staples 4, such that four rows 10 of staples 4 may be deployed on each side of the transection. In this way, fabrication of the feeder belts 2 may be simplified, because the same feeder belt 2 may be utilized multiple times without the need to fabricate a different configuration of feeder belt 2.

Figure 24:
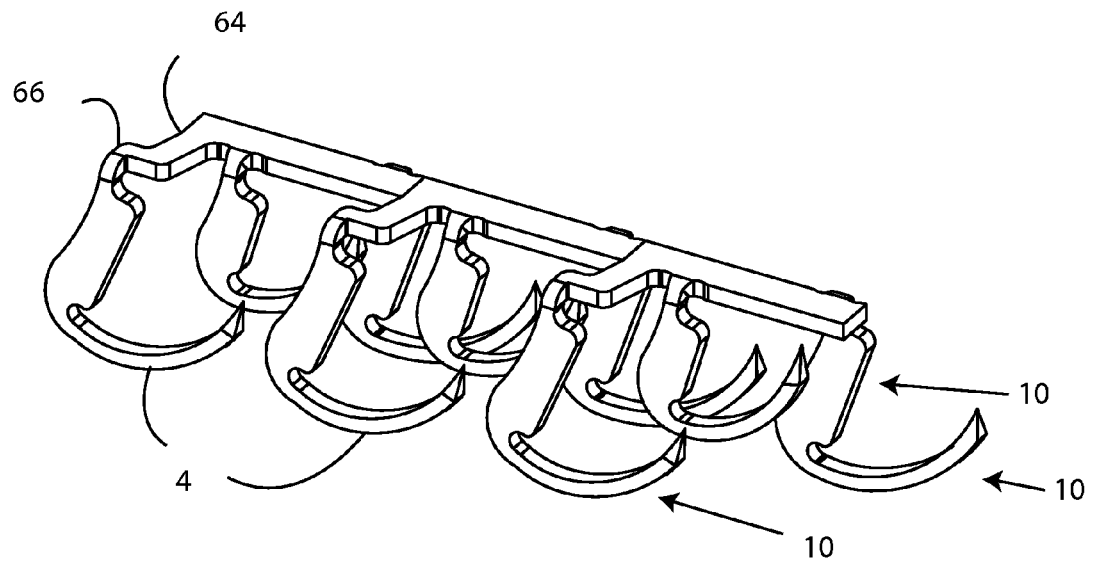
FIG. 24 is a perspective view of an exemplary feeder belt from which three rows of staples extend.

Alternately, three or more rows 10 of staples 4 may be attached to a single feeder belt 2. Referring also to FIG. 24, two rows 10 of staples 4 may be attached to the feeder belt 2 substantially as described in the Endocutter Document. A third row 10 may be provided by attaching staples 4 to the feeder belt 2 individually with extension arms 64. At least one extension arm 64 may extend generally laterally to the feeder belt 2, in a direction that may be substantially perpendicular to the longitudinal centerline of that feeder belt. At least one extension arm 64 may be substantially in the same plane as the corresponding feeder belt 2. Alternately, at least one extension arm 64 may be oriented or configured differently relative to the feeder belt 2. The staple 4 may be configured to be sheared off or otherwise separated from a lateral end 66 of the extension arm 64, such as by the three-dimensional wedge 20 of FIG. 4. Alternately, at least one extension arm 64 may be sheared off from or otherwise separated from the feeder belt 2, and may remain fixed to the staple 2. Advantageously, each extension arm 64 is connected to one corresponding staple 4. Alternately, at least one extension arm 64 may have two or more staples 4 connected thereto and extending therefrom. A staple 4 fixed to a corresponding extension arm 64 may be spaced laterally apart from the feeder belt 2.

Figure 25:
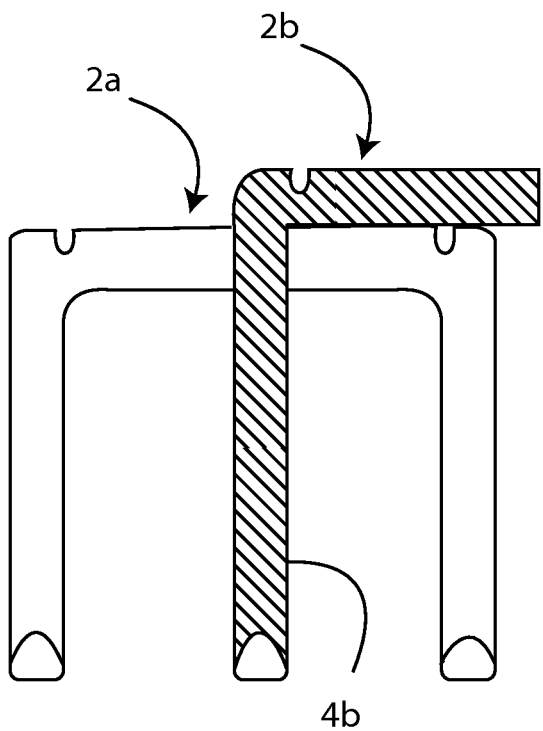
FIG. 25 is an end of an exemplary feeder belt assembly from which three rows of staples extend.
Figure 26:
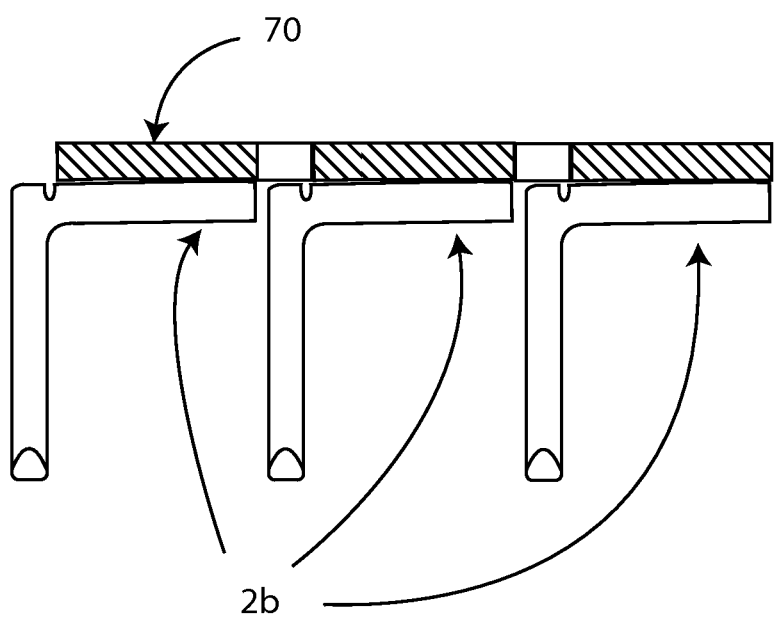
FIG. 26 is an end of another exemplary feeder belt assembly from which three rows of staples extend.

Alternately, a feeder belt 2 having three or more rows 10 of staples 4 attached to a single feeder belt 2 may be fabricated differently. As one example, referring to FIG. 25, a feeder belt 2a may be provided, along with a feeder belt 2b, such as described above with regard to FIG. 23. The feeder belt 2b may be generally L-shaped as viewed from the end. The feeder belt 2a may include a plurality of apertures therethrough. The feeder belt 2b may be fastened to an upper surface of the feeder belt 2a, such that the staples 4b of the feeder belt 2b extend through the apertures in the feeder belt 2a and beneath the feeder belt 2a. The feeder belt 2b may be fastened to the upper surface of the feeder belt 2a by laser welding or in any other suitable manner. Alternately, referring to FIG. 26, a master belt 70 may be provided, where one or more L-shaped feeder belts 2b are attached to the underside thereof by laser welding or in any other suitable manner. The master belt 70 need not have staples 4 extending therefrom, and may simply carry one or more L-shaped feeder belts 2b. Alternately, the master belt 70 may be fastened to one or more two-row feeder belts 2a. Alternately, the master belt 70 may include a plurality of apertures therethrough. At least one feeder belt 2b may be fastened to an upper surface of the master belt 70, such that the staples 4b of the feeder belt 2b extend through the apertures in the master belt 70 and beneath the feeder belt 70.

The feeder belts 2 described herein may be actuated such as described in this document, in the Endocutter Document, or in any other suitable manner. As another example, two-phase deployment may be used to deploy one or more staples 4. One or more wedges 20 or other deployment mechanisms may slide relative to one or more of the staples 4 in a first pass generally along one longitudinal direction. During the first pass, the one or more wedges 20 may deploy one or more staples 4 in part or in full. Those wedges 20 or other deployment mechanisms then may slide relative to one or more of the staples 4 in a second pass generally along the opposite longitudinal direction. During the second pass, the one or more wedges 20 may complete the deployment of any partially-deployed staples 4. Alternately, the first pass of the wedges 20 deforms the staples 4, and the second pass of the wedges shears the staples 4 from the feeder belt 2.

While the invention has been described in detail, it will be apparent to one skilled in the art that various changes and modifications can be made and equivalents employed, without departing from the present invention. It is to be understood that the invention is not limited to the details of construction, the arrangements of components, and/or the method set forth in the above description or illustrated in the drawings. Statements in the abstract of this document, and any summary statements in this document, are merely exemplary; they are not, and cannot be interpreted as, limiting the scope of the claims. Further, the figures are merely exemplary and not limiting. Topical headings and subheadings are for the convenience of the reader only. They should not and cannot be construed to have any substantive significance, meaning or interpretation, and should not and cannot be deemed to indicate that all of the information relating to any particular topic is to be found under or limited to any particular heading or subheading. Therefore, the invention is not to be restricted or limited except in accordance with the following claims and their legal equivalents.

What is claimed is:

1. A surgical apparatus, comprising:
   a feeder belt;
   a first plurality of staples fixed directly to and frangibly separable from said feeder belt;
   a plurality of extension arms extending at least partially in a lateral direction to a first distance from said feeder belt; and
   a second plurality of staples, each fixed to a corresponding said extension arm at a location spaced laterally apart from said feeder belt wherein a portion of each of said second plurality of staples extends at least partially in a lateral direction from said extension arm to a second distance from said feeder belt wherein said second distance is greater than said first distance.

2. The surgical apparatus of claim 1, wherein at least one said extension arm is fixed to and frangibly separable from said feeder belt.

3. The surgical apparatus of claim 1, wherein at least one said staple is fixed to and frangibly separable from the corresponding said extension arm.

4. The surgical apparatus of claim 1, further comprises a wedge configured to deploy at least one of the first plurality of staples or at least one of the second plurality of staples.

5. The surgical apparatus of claim 4, wherein the wedge is further configured to frangibly separate the at least one of the first plurality of staples from said feeder belt after said at least one of the first plurality of staples is deployed or the wedge is further configured to frangibly separate the at least one of the second plurality of staples from said extension arm after said at least one of the second plurality of staples is deployed or the wedge is further configured to frangibly separate the at least one of the second plurality of staples from said feeder belt after said at least one of the second plurality of staples is deployed.

6. The surgical apparatus of claim 4, wherein the wedge comprises two ramps wherein a first ramp configured to deploy the at least one of the first plurality of staples and a second ramp configured to frangibly separate the deployed at least one of the first plurality of staples from the feeder belt or wherein the wedge comprises two ramps wherein a first ramp configured to deploy the at least one of the second plurality of staples and a second ramp configured to frangibly separate the deployed at least one of the second plurality of staples from the extension arm or wherein the wedge comprises two ramps wherein a first ramp configured to deploy the at least one of the second plurality of staples and a second ramp configured to frangibly separate the deployed at least one of the second plurality of staples from the feeder belt.

7. The surgical apparatus of claim 6, wherein the first ramp being oriented laterally offset or laterally spaced apart from the second ramp.

8. The surgical apparatus of claim further comprises another wedge configured to frangibly separate the at least one of the first plurality of staples or the at least one of the second plurality of staples.

9. The surgical apparatus of claim 8, wherein said wedge being configured to slide in a first direction to deploy the staples, and wherein said another wedge being configured to slide in a second direction to frangibly separate the staples.

10. A surgical method, comprising:
providing a feeder belt, a plurality of staples fixed directly to and frangibly separable from said feeder belt, and at least one wedge slidable relative to said staples;
sliding at least one said wedge in a first direction relative to at least one said staple to deploy at least one staple at least in part;
sliding at least one said wedge in a second direction substantially opposite to said first direction; and
providing another plurality of staples wherein a portion of each of the another plurality of staples extends at least partially in a lateral direction from an extension arm.

11. The surgical method of claim 10, wherein said sliding at least one said wedge in a second direction completes the deployment of at least one said staple.

12. The surgical method of claim 10, wherein said sliding at least one said wedge in a first direction causes at least one said staple to deform, and wherein said sliding at least one said wedge in a second direction separates at least one said staple from said feeder belt.

13. A surgical apparatus, comprising:
a feeder belt;
a first plurality of staples fixed directly to and frangibly separable from said feeder belt;
a plurality of extension arms extending at least partially in a lateral direction away from said feeder belt;
a second plurality of staples, each fixed to a corresponding said extension arm at a location spaced laterally apart from said feeder belt wherein a portion of each of said second plurality of staples extends at least partially in a lateral direction from said extension arm;
a wedge; and
another wedge,
wherein said wedge being configured to slide in a first direction to deploy the staples, and wherein said another wedge being configured to slide in a second direction to frangibly separate the staples.

14. The surgical apparatus of claim 13, wherein at least one said extension arm is fixed to and frangibly separable from said feeder belt.

15. The surgical apparatus of claim 13, wherein at least one said staple is fixed to and frangibly separable from the corresponding said extension arm.

16. The surgical apparatus of claim 13, wherein said wedge is configured to deploy at least one of the first plurality of staples or at least one of the second plurality of staples.

17. The surgical apparatus of claim 16, wherein the wedge is further configured to frangibly separate the at least one of the first plurality of staples from said feeder belt after said at least one of the first plurality of staples is deployed or the wedge is further configured to frangibly separate the at least one of the second plurality of staples from said extension arm after said at least one of the second plurality of staples is deployed or the wedge is further configured to frangibly separate the at least one of the second plurality of staples from said feeder belt after said at least one of the second plurality of staples is deployed.

18. The surgical apparatus of claim 16, wherein the wedge comprises two ramps wherein a first ramp configured to deploy the at least one of the first plurality of staples and a second ramp configured to frangibly separate the deployed at least one of the first plurality of staples from the feeder belt or wherein the wedge comprises two ramps wherein a first ramp configured to deploy the at least one of the second plurality of staples and a second ramp configured to frangibly separate the deployed at least one of the second plurality of staples from the extension arm or wherein the wedge comprises two ramps wherein a first ramp configured to deploy the at least one of the second plurality of staples and a second ramp configured to frangibly separate the deployed at least one of the second plurality of staples from the feeder belt.

19. The surgical apparatus of claim 18, wherein the first ramp being oriented laterally offset or laterally spaced apart from the second ramp.

20. The surgical apparatus of claim 13, wherein said another wedge configured to frangibly separate at least one of the first plurality of staples or at least one of the second plurality of staples.

* * * * *